(12) United States Patent
Smith et al.

(10) Patent No.: US 7,459,600 B2
(45) Date of Patent: Dec. 2, 2008

(54) ISOLATION, SELECTION AND PROPAGATION OF ANIMAL TRANSGENIC STEM CELLS

(75) Inventors: Austin Gerard Smith, Cambridge (GB); Peter Scott Mountford, Melbourne (AU)

(73) Assignee: The University of Edinburgh, Edinburgh (GB)

( * ) Notice: Subject to any disclaimer, the term of this patent is extended or adjusted under 35 U.S.C. 154(b) by 0 days.

(21) Appl. No.: 11/832,165

(22) Filed: Aug. 1, 2007

(65) Prior Publication Data

US 2008/0026459 A1      Jan. 31, 2008

Related U.S. Application Data

(63) Continuation of application No. 11/084,154, filed on Mar. 21, 2005, now Pat. No. 7,256,041, which is a continuation of application No. 09/537,562, filed on Mar. 30, 2002, now Pat. No. 6,878,542, which is a continuation of application No. 08/535,141, filed on Dec. 29, 1995, now Pat. No. 6,146,888.

(30) Foreign Application Priority Data

Apr. 21, 1993   (GB)   ................................ 9308271.7
Apr. 21, 1994   (WO)   ...................... PCT/GB94/00848

(51) Int. Cl.
*A01K 67/00*     (2006.01)
*A01K 67/033*    (2006.01)
*C12N 15/00*     (2006.01)

(52) U.S. Cl. ............................... 800/8; 800/18; 435/455
(58) Field of Classification Search .................... 800/21; 435/455

See application file for complete search history.

(56) References Cited

U.S. PATENT DOCUMENTS

| 5,112,767 A | 5/1992 | Roy-Burman et al. |
| 5,733,727 A | 3/1998 | Field |
| 6,015,671 A | 1/2000 | Field |
| 6,146,888 A | 11/2000 | Smith et al. |

FOREIGN PATENT DOCUMENTS

| EP | 0 235 113 | 9/1987 |
| WO | WO 90/01541 | 2/1990 |
| WO | WO 91/01140 | 2/1991 |
| WO | WO 92/11355 | 7/1992 |
| WO | WO 95/14079 | 5/1995 |

OTHER PUBLICATIONS

Definition of "murine" from Life Science Dictionary. 2008.*
Apperley et al., Blood, 78(2) pp. 310-317 (1991).
Beddington et al., "An In Situ Transgenic Enzyme Marker For the Midgestation Mouse Embryo and the Visualization of Inner Cell Mass Clones During Early Organogenesis," Development, 106:37-46 (1989).
Beresford, J. N., "Osteogenic Stem Cells and the Stromal System of Bone and Marrow" Osteogenic Stem Cells, No. 240:270-280 (1989).
Bongso et al., "The Growth of Inner Cell Mass Cells From Human Blastocysts," Theriogenology, 41:167 (1994).
Bradley, Bio/technology, vol. 10, pp. 534-539 (1992).
Campbell et al., "Transplantation of Cultured Small Bowel Enterocytes," Gut, 34:1153-1155 (1993).
Cattaneo et al., "Proliferation and Differentiation of Neuronal Stem Cells Regulated by Nerve Growth Factor," Nature, 347:762-765 (1990).
Cattaneo, E., et al., "Identifying and Manipulating Neuronal Stem Cells" TINS, vol. 14, No. 8,:338-340 (1991).
Doetschman et al., "The in vitro Development of Blastocyst-Derived Embryonic Stem Cell Lines: Formation of Visceral Yolk Sac, Blood Islands and Myocardium," J. Embryol. expl. Morph., 87:27-45 (1985).
Doetschman, T., et al., "Establishment of Hamster Blastocyst-Derived Embryonic Stem (ES) Cells" Developmental Biology, vol. 27:224-227, (1988).
Evans et al., "Establishment in Culture of Pluripotential Cells From Mouse Embryos," Nature, 292:154-156 (1981).
First et al., "Systems for Production of Calves from Cultured Bovine Embryonic Cells," Reprod. Fertil. Dev., 6:553-562 (1994).
Friedrich et al., "Promoter Traps in Embryonic Stem Cells: A Genetic Screen to Identify and Mutate Developmental Genes in Mice," Genes & Devel., 5:1513-1523 (1991).
Ghattas et al., "The Encephalomyocarditis Virus Internal Ribosome Entry Site Allows Efficient Coexpression of Two Genes From a Recombinant Provirus in Cultured Cells and in Embryos," Molecular and Cellular Biol., 11:5848-5859 (1991).
Glazko, "Early Adventures in Drug Metabolism. 3. Chloramphenicol," Therapeutic Drug Monitoring, 9:320-330 (1987).
Graves et al., "Derivation and Characterization of Putative Pluripotential Embryonic Stem Cells From Preimplantation Rabbit Embryos," Mol. Reprod. & Devel., 36:424-433 (1993).
Hooper et al., HPRT-Deficient (Lesch-Nyhan) Mouse Embryos Derived From Germline Colonization By Cultured Cells, Nature, 326:292-295 (1987).
Ishihara, et al., "A cell-Based Assay for Evaluating the Interaction of Heparin-like Molecules and Basic Fibroblast Growth Factor," Analytical Biochemistry, vol. 202(2) 310-315 (1992).
Kohn, Current Opinion in Pediatrics, vol. 7, pp. 56-63 (1995).
Kroon et al., "Antibacterial Drugs and Their Interference With the Biogenesis of Mitochondria in Animal and Human Cells," Pharmaceutisch Weekblad Scientific Edition, 5:81-87 (1983).
Martin, "Isolation of a Pluripotent Cell Line From Early Mouse Embryos Cultured in Medium Conditioned By Teratocarcinoma Stem Cells," Proc. Natl. Acad. Sci. USA, 78:7634-7638 (1981).

(Continued)

Primary Examiner—Michael C. Wilson
(74) Attorney, Agent, or Firm—Finnegan, Henderson, Farabow, Garrett & Dunner, LLP

(57) ABSTRACT

Animal stem cells are obtained and maintained by culturing cells containing, in the genome, a selectable marker. Differential expression of the selectable marker enables preferential survival and/or division of the desired stem cells compared to the non-stem cells.

12 Claims, 2 Drawing Sheets

OTHER PUBLICATIONS

Meyers et al., "Transfection of the Hypotrichous Ciliate Stylonychia lemnae With Linear DNA Vectors," Gene, 63:31-40 (1988).

Mountford et al., "Dicistronic Targeting Constructs: Reporters and Modifiers of Mammalian Gene Expression," Proc. Natl. Acad. Sci. USA, 91:4303-4307 (1994).

Mullins et al., J. Clin. Invest., vol. 98, pp. S37-S40 (1996).

Nichols et al., "Establishment of Germ-Line-Competent Embryonic Stem (ES) Cells Using Differentiation Inhibiting Activity," Development, 110:1341-1348 (1990).

Notarianni et al., "Maintenance and Differentiation in Culture of Pluripotential Embryonic Cell Lines from Pig Blastocysts," J. Repord. Fert., Suppl., 41:51-56 (1990).

Notarianni, E., et al., "Derivation of Pluripotent, Embryonic Cell Lines from the Pig and Sheep" J. Reprod. Fert. Suppl. 43:255-260 (1991).

O'Gorman, S., et al., "Recombinase-Mediated Gene Activation and Site-Specific Integration in Mammalian Cells" Science, vol. 251:1351-1355 (1991).

Okamoto, K. et al., "A Novel Octamer Binding Transcription Factor is Differentially Expressed in Mouse Embryonic Cells," Cell, vol. 60, pp. 461-472 (1990).

Okazawa et al., The EMBO, vol. 10, pp. 2997-3005 (1991).

Okazawa, H. et al., "The oct3 gene, a gene for an embryonic transcription factor, is controlled by a retinoic acid repressible enhancer," EMBO J. 10(10), pp. 2997-3005 (1991).

Parkinson, E., "Epidermal Keratinocyte Stem Cells: Their Maintenance and Regulation" Cell Biology, vol. 3:435-444 (1992).

Pelletier et al., "Internal Initiation of Translation of Eukaryotic mRNA Directed By a Sequence Derived From Poliovirus RNA," Nature, 334:320-325 (1988).

Pera, M.F., et al., "Isolation and Characterization of a Multipotent Clone of Human Embryonal Carcinoma Cells" Differentiation, vol. 42:10-23 (1989).

Petropoulos et al., J. Virology, vol. 66, pp. 3391-3397 (1992).

Resnick et al., "Long-term Proliferation of Mouse Primordial Germ Cells in Culture," Nature, 359:550-551 (1992).

Rudland, P.S., et al., "Morphogenetic Behavior of Simian Virus 40-Transformed Human Mammary Epithelial Stem Cell Lines on Collagen Gels" In Vitro Cell Dev. Biol., vol. 27A,:103-112, (Feb. 1991).

Saito, S., et al., "Bovine Embryonic Stem Cell-Like Cell Lines Cultured Over Several Passages" Roux's Arch. Dev. Biol., vol. 201:134-141 (1992).

Schoeler et al., "New Type of POU Domain in Germ Line-Specific Protein Oct-4," Nature, 344:435-439 (1990).

Schoeler et al., "Octamer Binding Proteins Confer Transcriptional Activity In Early Mouse Embryogenesis," The EMBO Journal, 8:2551-2557 (1989).

Schoeler, H.R., "Octomania: The POU factors in murine development," Trends Genet. 7(10), pp. 323-329 (1991).

Schoeler, TIG, vol. 7, pp. 323-329 (1991).

Skarnes et al., "A Gene Trap Approach in Mouse Embryonic Stem Cells: the lacZ Reporter is Activated by Splicing Reflects Endogenous Gene Expression, and Is Mutagenic in Mice," Genes & Devel., 6:903-918 (1992).

Smith, "Culture and Differentiation of Embryonic Stem Cells," J. Tiss. Cult. Meth., 13:89-94 (1991).

Stutzmann, J., et al., "Bone Cell Histogenesis: The Skeletoblast as a Stem-Cell for Preosteoblasts and for Secondary-Type Prechondroblasts," Factors and Mechanisms Influencing Bone Growth, pp. 29-43 (1982).

Sukoyan et al., "Embryonic Stem Cells Derived From Morulae, Inner Cell Mass, and Blastocysts of Mink: Comparisons of Their Pluripotencies," Mol. Reprod. & Devel., 36:148-158 (1993).

Sukoyan, M.A., et al., "Isolation and Cultivation of Blastocyst-Derived Stem Cell Lines from American Mink (*Mustela vison*)," Mol. Reprod. Dev., vol. 33:418-431(1992).

Sutherland et al., "Functional Characterization of Individual Human Hematopoietic Stem Cells Cultured at Limiting Dilution on Supportive Marrow Stromal Layers," Proc. Natl. Acad. Sci. USA, 87:3584-3588 (1990).

Tait et al., "Colonic Mucosal Replacement by Syngeneic Small Intestinal Stem Cell Transplantation," The American Journal of Surgery, 167:67-72 (1994).

Takeda, J. et al., "Human Oct 3 gene family: cDNA sequences, alternative splicing, gene organization, chromosomal location, and expression at low levels in adult tissues," Nucleic Acids Res. 20(17), pp. 4613-4620 (1992).

Terstappen et al., "Sequential Generations of Hematopoietic Colonies Derived From Single Nonlineage-Committed $CD34^+CD38^-$ Progentor Cells," Blood, 77:1218-1227 (1991).

Treisman, "Transient Accumulation of c-fos RNA Following Serum Stimulation Requires a Conserved 5' Element and c-fos 3' Sequences," Cell, 42:889-902 (1985).

Watt, F., "Epidermal Stem Cells in Culture," J.Cell Sci., Suppl. 10:85-94 (1988).

Wheeler, "Development and Validation of Swine Embryonic Stem Cells: A Review," Reprod. Fertil. Dev., 6:563-568 (1994).

Whitehead, R. H., et al., "A New Human Breast Carcinoma Cell Line (PMC42) With Stem Cell Characteristics. II. Characterization of Cells Growing as Organoids," JNCI, vol. 71, No. 6:1193-1203 (1983).

Yang et al., "Upper Human Hair Follicle Contains a Subpopulation of Keratinocytes with Superior In Vitro Proliferative Potential," J. Invest. Dermatol., 101:652-659 (1993).

Yoshida et al., "Maintenance of the Pluripotential Phenotype of Embryonic Stem Cells Through Direct Activation of gp130 Signaling Pathways," Mechanisms of Development, 45:163-171 (1994).

\* cited by examiner

ISOLATION, SELECTION AND PROPAGATION OF ANIMAL TRANSGENIC STEM CELLS

This is a continuation of application Ser. No. 11/084,154, filed Mar. 21, 2005, now U.S. Pat. No. 7,256,041, which is a continuation of application Ser. No. 09/537,562, filed Mar. 30, 2002, now U.S. Pat. No. 6,878,542, which is a continuation of application Ser. No. 08/535,141, filed Dec. 29, 1995, now U.S. Pat. No. 6,146,888, all of which are incorporated herein by reference.

This invention relates to methods of isolating and/or enriching and/or selectively propagating animal stem cells, genetically modified animal cells and animals for use in said method, transgenic animals providing a source of such cells and selectable marker constructs for producing genetically modified cells and transgenic animals.

Stem cells are progenitor cells which have the capacity both to self-renew and to differentiate into mature somatic tissues.

Embryonic stem cells are the archetypal stem cell, being capable of differentiating to form the whole gamut of cell types found in the adult animal. Such stem cells are described as pluripotential as they are capable of differentiating into many cell types. Other types of stem cells, for example bone marrow stem cells and epidermal stem cells, persist in the adult animal. These stem cells have a more restricted capacity for differentiation.

In general, when required for research purposes or for medical use, stem cells have to be isolated from tissue samples by various fractionation procedures, but even after careful segregation of cell types, these stem cell preparations consist of mixed cell types and while enriched for stem cells, include high proportions of differentiated cells which are not categorised as stem cells.

Furthermore, most stem cells cannot be grown readily in culture and when attempts are made to culture stem cells, the cells being cultured (which ordinarily contain a mixed population of cell types) grow at different rates and stem cells rapidly become overgrown by non-stem cell types. An exception is that embryonic stem cells from two specific strains of mice (129 and Black 6) can be cultured in vitro. Thus established lines of embryonic stem cells can be obtained by culturing early (3½ day) embryonic cells from murine strain 129 and Black 6, or hybrids thereof.

There has developed a pressing need to isolate and maintain in vitro embryonic stem cells from other murine strains and more especially from other species including other laboratory animals (e.g. rats, rabbits and guinea pigs), domesticated animals (e.g. sheep, goats, horses, cattle, pigs, birds, fish, etc.) and primates. Similarly, numerous medical applications for other pluripotential cells such as haematopoietic stem cells also demand their isolation and culture in vitro.

However hitherto the problems associated with producing cultures of stem cells including the problem of producing cell populations of a satisfactorily low degree of heterogeneity and the problem of overgrowth in culture of non-pluripotent cells have not been solved. A particular problem associated with the continuing presence of certain differentiated cell types is that these can cause elimination of stem cells from the culture by inducing their differentiation or programmed cell death.

We have now developed a technique by which the aforementioned problems can be overcome.

According to one aspect of the invention there is provided a method of isolating and/or enriching and/or selectively propagating animal stem cells, which comprises maintaining a source of said cells under culture conditions conducive to cell survival, characterised in that the source of cells includes cells containing a selectable marker which is capable of differential expression in (a) stem cells and (b) cells other than the desired stem cells, whereby differential expression of said selectable marker results in preferential isolation and/or survival and/or division of the desired stem cells. In the context of this invention, the term "animal cell" is intended to embrace all animal cells, especially of mammalian species, including human cells.

Examples of stem cells include both unipotential and pluripotential stem cells, embryonic stem cells, gonadal stem cells, somatic stem/progenitor cells, haematopoietic stem cells, epidermal stem cells and neuronal stem cells.

In carrying out the method of the invention, the source of cells may include pluripotential cells having a positive selectable marker and expression of the said marker is used to permit isolation and maintenance of the pluripotential cells. Alternatively, the source of cells may include a negative selectable marker which is expressed in cells other than the desired pluripotential cells and is used selectively to deplete the source of cells other than the desired pluripotential cells.

The selectable marker may, for example, be a foreign gene, a cellular gene or an antibiotic resistance gene such as for example the bacterial neomycin resistance gene.

Alternatively the selectable marker may be a growth stimulating gene, for example an immortalising gene, an oncogene or a gene coding for the polyoma or SV40 T antigens or derivatives thereof, or the selectable marker may be a gene coding for a growth factor or a growth factor receptor or a signal transducing molecule or a molecule that blocks cell death.

In one particular embodiment the isolation and/or enrichment and/or selective propagation of the desired pluripotential cells is dependent on the presence of cells other than the desired pluripotential cells and the simultaneous maintenance of both cell types is dependent on expression of a selectable marker, in one or the other cell population, which is capable of rescuing cells that do not express the marker but which neighbour cells which do themselves express the marker. In this instance, the selectable marker may, for example, be the hypoxanthine phosphoribosyl tranferase (HPRT) gene.

In another embodiment the selectable marker may be a gene encoding a product which is toxic per se, or a toxic gene product which is conditionally active in combination with a suicide substrate. An example of such a gene product is a herpes simplex virus thymidine kinase (HSV-TK) in combination with ganciclovir.

Expression of the selectable marker may be achieved by operatively inserting the selectable marker into an expression construct prior to introduction to the cell source, in which case expression of the selectable marker can result from the introduction of either a stable or transiently integrated construct. Alternatively, expression of the selectable marker results from operatively inserting the selectable marker into an endogenous gene of the cell source.

Various means of introducing the selectable marker may be employed, including introduction into the cells by transfection, lipofection, injection, ballistic missile, viral vector or by electroporation.

The source of the cells may be a single cell such as a fertilized oocyte, or it may comprise a mixture of cells, such as cells derived from an embryo, blood or somatic tissue of a normally bred or transgenic animal or cell line. In the latter case the selectable marker may be incorporated into the transgenic animal's genome.

Most preferably, in carrying out the method of the invention a gene or gene fragment operatively linked to and regulating expression of the selectable marker is/are associated with a pluripotential stage of cellular development. Such a gene or gene fragment may be active in pluripotential cells of the developing embryo, especially in the inner cell mass and/or primitive ectoderm, or may be active in adult stem cells.

In preparing a source of cells for use in accordance with the invention one of the following protocols may advantageously be adopted:

introducing into a source of cells containing stem cells, a selectable marker construct, wherein said selectable marker construct is adapted to operatively link to an endogenous gene which provides said differential expression, or introducing into a source of cells containing stem cells, a selectable marker construct, wherein said selectable marker construct has been previously linked to one or more gene fragments which provide said differential expression.

The genetic marker preferably comprises a selectable marker operatively linked to a promoter which is differentially active in the desired pluripotent cells (e.g. primitive ectoderm). By "selectable marker" is meant a selectable gene which may be a foreign gene or a cellular gene which is not naturally expressed, or such a gene which is naturally expressed, but at an inappropriate level, in the target cell populations. This gene in use acts as a selection marker by adapting the phenotype of the target cell population in such a way that cells with the so-adapted phenotype may be enriched or depleted under particular culture conditions.

In the case where stem cells are embryonic cells it is preferred that the selectable marker is operatively linked to a promoter which is differentially active in stem (e.g. primitive ectoderm, primordial germ cells) and non-stem cells. Promoter and other cis-regulatory elements may be included in the expression construct prior to introduction into the cells or by targeting promoter-less constructs into specific genes by site specific recombination.

A wide variety of gene products may be relied upon for selective isolation and propagation of the desired stem cells, including markers which are designed to protect the desired cells from the effects of an inhibiting factor present in the culture medium. In this instance, the inhibiting factor can, for example, be an antibiotic substance which inhibits growth or reproduction of cultured cells, not expressing the gene (i.e. cells other than the desired cells). The selectable marker (e.g. HPRT) may also provide protection both for the desired cells in which it is expressed as well as other closely associated cells by means of metabolic rescue.

Alternatively the selectable marker may selectively permit the growth of stem cells. In this instance the marker may encode a growth factor, a growth factor receptor, a transcription factor, an immortalising or an oncogenic product (e.g. temperature sensitive simian virus 40 T antigen).

Alternatively, the selectable marker may be a cell surface antigen or other gene product which allows purification or depletion of expressing cells for example by panning or fluorescence-activated cell sorting (FACS). The invention thus enables stem cell populations to be obtained/maintained having a satisfactory degree of homology.

Alternatively the selectable marker may be a conditionally toxic gene for instance herpes simplex virus thymidine kinase [HSV-TK]. In this instance expression of the selectable marker is directed to cells other than the desired cells and not to stem cells. Cells other than the desired phenotype may be selectively depleted by addition of a lethal substrate (e.g. ganciclovir).

The genetic marker may be introduced into the source of cells by a variety of means, including injection, transfection, lipofection, electroporation or by infection with a viral vector.

Further, the source of cells may be produced by transfection extemporaneously, or the source of cells may be derived from a transgenic animal, e.g., the founder transgenic animal or an animal at least one ancestor of which has had the aforementioned genetic marker introduced into its genetic complement. In such transgenic animals it is possible for the marker to pass down the germ line and eventually results in the production of progeny, from the tissues of which (especially from the embryonic tissue) the required source of cells can be derived.

Thus according to further aspects of the invention, there is provided an animal cell capable of being cultured under appropriate selective culture conditions so as to enable isolation and/or enrichment and/or selective propagation of stem cells, characterised in that said cell contains a selectable marker wherein differential expression of the selectable marker in (a) the desired stem cells and (b) cells other than the desired stem cells enables selective growth of the desired stem cell to occur.

The invention further provides an animal cell capable of being cultured under selective culture conditions so as to grow as stem cells, characterised in that said cells contain stem cells containing a genetic marker, whereby a gene product associated with the genetic marker is produced and which under said culture conditions causes selective survival and/or division of the desired stem cells to occur.

The animal cells according to this aspect of invention are preferably characterised by possessing the preferred characteristics described above.

The invention further provides according to another aspect thereof, a transgenic animal having genetic characteristics such that it or its progeny, during embryonic development or later life, constitute a source of animal pluripotential cells as defined above.

Such transgenic animal may be produced according to the invention by introducing a genetic marker into a fertilised oocyte or an embryonic cell, or an embryonic stem cell in vitro the genetic marker having the characteristics defined above, and utilising the resulting transformed oocyte or embryonic cell as a progenitor cell for the desired transgenic animal.

Vectors for use in producing an animal cell defined above form a further aspect of the invention.

Thus the invention further provides vectors for use in genetically modifying animal cells so as to produce transformed cells suitable for use as the source of cells for the method referred to above, said vector comprising a first genetic component corresponding to said selectable marker and a second genetic component which in the genetically modified animal cells (1) results in the said differential expression of the selectable marker from either a transiently or stably integrated construct or (2) enables site-directed integration of the selectable marker into a specific gene so as to provide operative coupling of the selectable marker with targeted endogenous gene regulatory elements.

Such vectors may be in the form of expression vectors in which said second genetic component includes control sequences which are differentially activated (a) in stem cells and (b) in cells other than the desired stem cells.

The invention covers vectors which when used to transform animal cells become integrated into the animal genome as well as vectors which do not become so integrated.

The expression vectors referred to above may comprise a DNA sequence coding for the afore-mentioned selectable marker operatively linked to a genetic control element, or sequence enabling targeting of a promoterless marker to an endogenous gene which is expressed differentially in the said stem cells and in cells other than the desired stem cells.

For the generation of pluripotential embryonic stem cells the expression constructs preferably comprise a DNA sequence coding for said selectable marker operatively linked or targeting to a genetic control element(s) which is associated with a stage of embryonic development prior to differentiation of pluripotential embryonic cells. Most preferably the genetic control elements derive from a gene specifically active in the inner cell mass of the mouse blastocyst, in primitive ectoderm, and in primordial germ cells of the early embryo.

In more detail, the present invention has resulted in the development of expression constructs which direct specific expression of selectable markers in stem cells and not in differentiated cell types. Having introduced an expression construct by transfection or via the generation of transgenic animals, stem cells present within mixed cell populations can be isolated by culturing in the presence of the selection agent in vitro, or by otherwise manipulating the culture conditions.

One example of a gene which displays a suitably restricted stem cell expression pattern and therefore may provide suitable "stem cell specific" regulatory elements for the expression of a selectable marker in accordance with the invention is the Oct4 gene.

Octamer binding transcription factor 4 is a member of the POU family of transcription factors (reviewed by Schöler, 1991). Oct4 transcription is activated between the 4- and 8-cell stage in the developing mouse embryo and it is highly expressed in the expanding blastocyst and then in the pluripotent cells of the egg cylinder. Transcription is down-regulated as the primitive ectoderm differentiates to form mesoderm (Schöler et al., 1990) and by 8.5 d.p.c. (days post coitum) is restricted to migrating primordial germ cells. High level Oct4 gene expression is also observed in pluripotent embryo carcinoma and embryonic stem cell lines, and is down-regulated when these cells are induced to differentiate (Schöler et al., 1989; Okamoto et al., 1990).

Selectable marker genes under the control of the Oct4 promoter may, according to the invention, be applied to the isolation of embryonic stem cell lineages. Furthermore, reports describing low level Oct4 expression in some adult tissues (Takeda et al., 1992) may extend the utility of these expression constructs beyond embryonic stem cells to include other stem cells essential to tissue homeostasis and repair in other systems including the haematopoietic system. In the event that Oct4 is not expressed in somatic stem cells, other transcriptional regulatory elements, such as those associated with the haematopoietic stem cell specific antigen CD34, may be utilised in a similar manner.

Two specific approaches are provided according to the invention for generating the desired spatial and temporal restrictions in transgenic expression. The first approach is through the generation of transgenic animals in which a partially characterised Oct4 gene promoter fragment (Okazawa et al., 1991) is employed to drive stem cell specific transcription of the selectable marker. An appropriate selectable marker is the neomycin phosphotransferase gene which confers resistance to the antibiotic G418. An alternative is to utilise a selectable marker which is associated with the production of a gene product which can counteract a deficiency in a metabolite, e.g. the hypoxanthine-guanine phosphoribosyl transferase (HPRT) gene in HPRT-deficient cells (Hooper et al., 1987). This approach may be advantageous in situations where stem cells require continuous support from closely associated differentiated cells. In this instance direct cell contact will permit metabolic rescue of the neighbouring support cells by the stem cells despite the lack of selectable marker gene expression in the support cells.

The second approach utilises the endogenous Oct4 gene locus, and therefore the associated Oct4 gene regulatory elements, to link resistance marker gene expression as closely as possible with the endogenous Oct4 gene expression profile. This may be accomplished by high efficiency gene trap targeted mutagenesis of the Oct4 gene in embryonic stem cells. This approach provides more tightly regulated control of selectable marker gene expression by avoiding random integration site effects which often result in unpredictable expression patterns of randomly integrated constructs.

EXAMPLE 1

1. Isolation of OCT4 Promoter Sequences:

We screened a strain 129 mouse genomic lambda library with a 330 bp 5'Oct4 cDNA fragment. Several clones were isolated and screened by restriction analysis and Southern blot hybridization. A 1.4 kb Bam HI-Hind III fragment containing the Oct4 promoter element (Okazawa et al., 1991) was isolated from clone 1 and ligated into pBluescript II KS(−) (Stratagene) to generate pOct4 (5' genomic).

Figure 1:
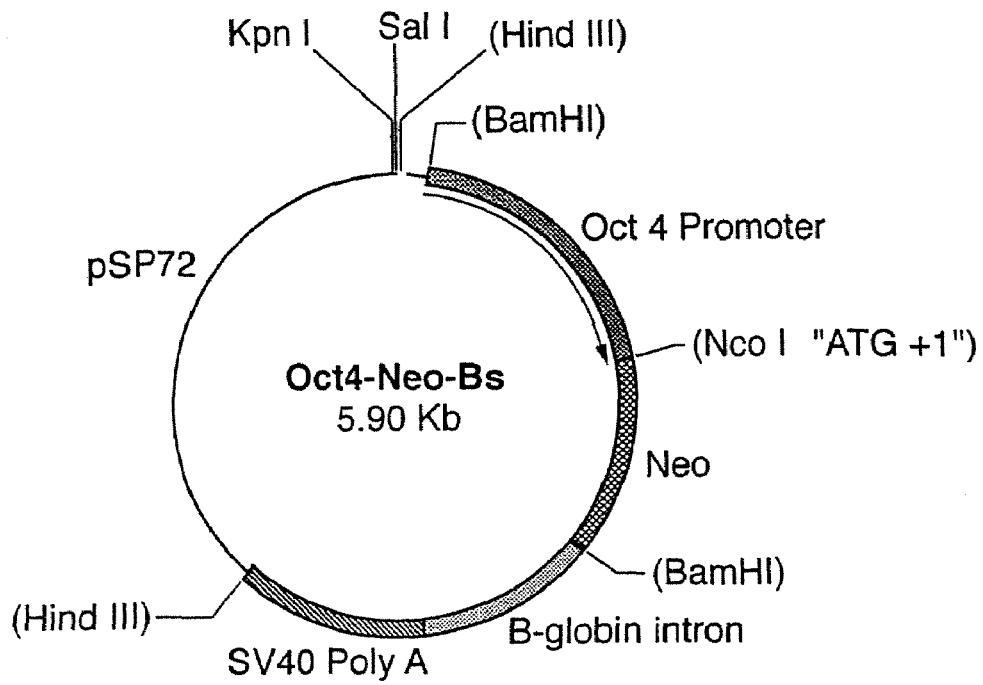
FIG. 1 illustrates the structure of plasmid Oct-4-Neo-βS.
Figure 2:
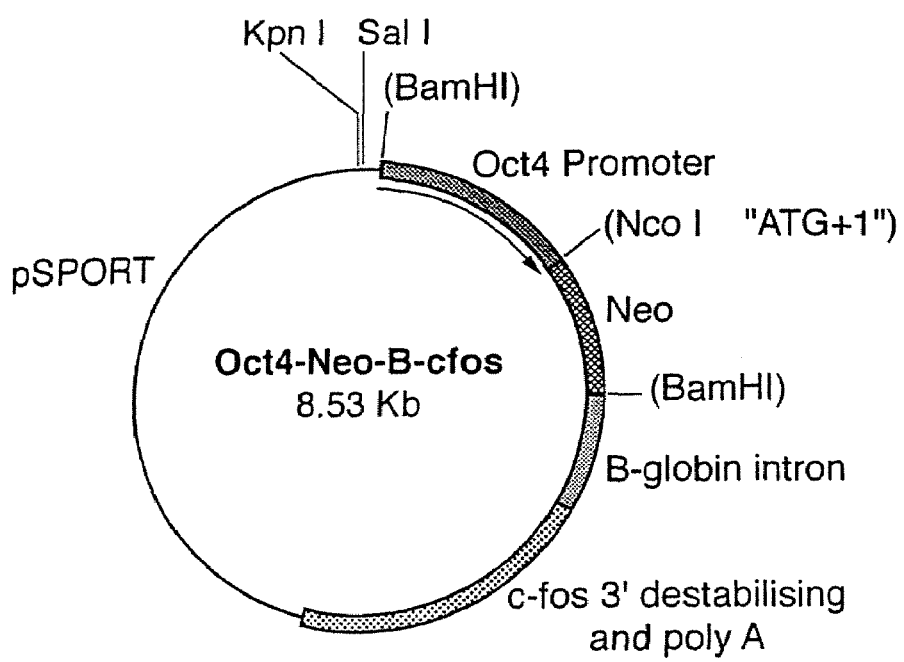
FIG. 2 illustrates the structure of plasmid Oct-4-Neo-βfos.

2. Construction of Plasmids:

To generate the Oct4-Neo promoter constructs an engineered Neomycin resistance gene (neo), designed to provide an Nco I restriction site at the translation initiation codon, was isolated from pLZIN (Ghattas et al., 1991) as a 1.1 kb Xba I-Sph I fragment encompassing encephalomyocarditis virus internal ribosome entry site sequence (EMCV-IRES, Ghattas et al., 1991) and 5'-Neo coding sequences and cloned into pSP72 (Promega Biotech). The Kpn I-Nco I EMCV-IRES sequence was replaced with a 1.3 kb Oct4 promoter fragment isolated from pOct4 (5'genomic) by Kpn I and subsequent partial Nco I restriction digest. Neo3'-coding, rabbit β-globin gene (intron) and SV40 polyadenylation sequences were isolated as a 1.7 kb Sph I fragment from 6P-IRESNeo-βS and ligated into the Sph I site to generate Oct4-Neo-βS (FIG. 1). To generate the Oct4-Neo-fos construct (FIG. 2), an Oct4-Neo-βS Bam HI fragment incorporating the Oct4 promoter, neo gene and the rabbit β-globin intron was inserted 5' to a human c-fos genomic sequence. This 1.7 kb genomic sequence (Bal I-Sph 1) encodes human c-fos mRNA 3' coding and no-coding sequences previously associated with mRNA destabilization (Wilson and Triesman, 1988), and, the c-fos polyadenylation sequence.

Figure 3:
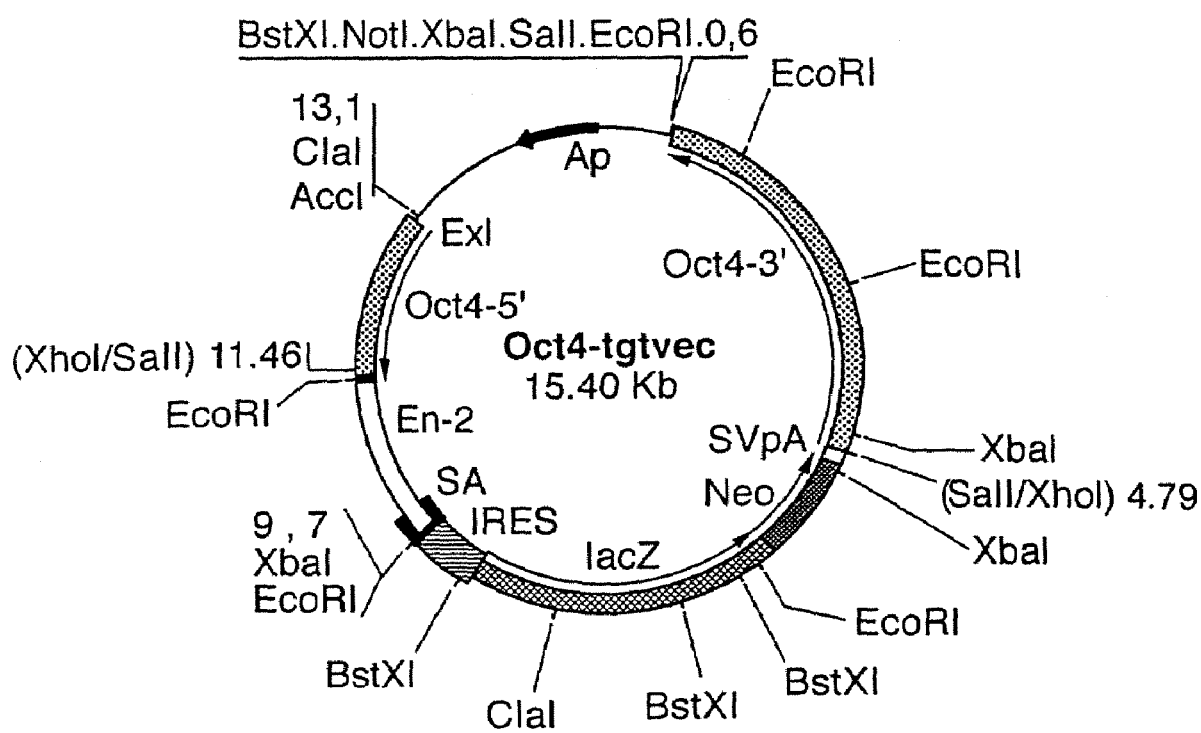
FIG. 3 illustrates the structure of the plasmid Oct-4-tgtvec.

The Oct4-neo construct (Oct4-tgtvec) is designed for targetted integration into the Oct4 gene (FIG. 3). The Oct4 targetting construct contains 1.7kb of 5'Oct4 gene sequence and 4.2 kb of 3'Oct4 gene sequence. Following homologous recombination this construct incorporates a IacZ-neomycin fusion gene (βgeo, encoding a bifunctional protein, Freidrich and Soriano, 1991) into the first intron of the Oct4 gene.

Splicing from the splice donor sequence of the first exon-intron boundary to the integrated IRES-βgeo sequence is facilitated by the inclusion of a murine engrailed-2 splice acceptor sequence (Skarnes et al., 1992) immediately 5' to the IRES-βgeo sequence. Translation of the βgeo cistron of the Oct4-βgeo fusion transcript is facilitated by the inclusion of the EMCV-IRES immediately 5' to the βgeo coding sequence.

3. ES Cell Transfection and Colony Selection:

Mouse 129 ES cells (line CGR-8) were prepared and maintained in the presence of Differentiation Inhibiting Activity (DIA) or Leukemia Inhibitory Factor (LIF) as described by Smith (1991). Plasmid DNA for transfection was linearised by Sal I digest, ethanol precipitated and resuspended at 10-14 mg/ml in PBS. Following 10 hours culture in fresh medium, near confluent ES cells were dispersed by trypsinisation, washed sequentially in culture medium and PBS, and resuspended at $1.4 \times 10^8$/ml in PBS for immediate transfection. Routinely, 0.7 ml of cell suspension was mixed with 0.1 ml DNA containing solution and electroporated at 0.8 kV and 3.0 µFD using a Biorad Gene Pulser and 0.4 cm cuvettes. Transfections were plated on gelatinised tissue culture dishes at $5-8 \times 10^4$/cm$^2$ in growth medium for 16 hours prior to the addition of selection medium containing 200 µg/ml (active) G418 (Sigma). Single colonies were picked 8-10 days post-transfection and transferred in duplicate into 24 well tissue culture plates for further expansion in growth medium containing 200 µg/ml G418.

Clonal cell lines bearing the Oct4-Neo-βS and Oct4-Neo-fos constructs (referred to as Oct4-Neo cell lines) were grown for two days, washed twice with PBS and the medium replaced with fresh G418 medium with or without DIA. Cell lines which grew normally in the presence of DIA but did not survive in the absence of DIA were selected for expansion and further analysis.

Clonal cell lines bearing the Oct4-tgtvec targetting construct (referred to as Oct4-targetted cell lines) were expanded in duplicated 24 well plates. Once confluent, one series of cells were frozen for storage while the remainder were analysed by Southern analysis.

4. Further Characterisation of Oct4-Neo and Oct4-Targetted Cell Lines:

Selected Oct4-Neo cell lines were assayed for ES cell growth and differentiation in DIA supplemented or non-supplemented medium at various G418 concentrations. Cells were plated at $1 \times 10^4$/cm$^2$ in 12 well tissue culture plates in the various media preparations and cultured for 6 days. Fresh medium was applied every 2 days until day 6 when cells were fixed and stained as previously described (Smith, 1991.) Oct4-targetted cell lines positive by genomic Southern analysis were analysed by lacZ staining and growth and differentiation in DIA supplemented or non-supplemented medium in 2OOpg/ml G418.

5. Production of Embryoid Bodies from Oct4-Neo Cell Lines:

Embryoid bodies were generated by the hanging drop method (Hole and Smith, in press) and maintained in suspension culture for 2, 4, 6 or 8 days in the presence or absence of G418. Control embryoid bodies were generated from the parental cell line CGR-8 in the absence of G418. Embryoid bodies were then collected and transferred to gelatinised tissue culture dishes to enable adherence and expansion of the aggregates for analysis of contributing cell types. All embryoid bodies were maintained for 4 days in the absence of DIA and G418 prior to inspection.

6. Production of Chimeras from Oct4-Neo and Oct-4 Targetted Cell Lines:

Selected Oct4-Neo cell lines were cultured in the absence of G418 for 7 days prior to embryo injection as previously described (Nichols et al., 1990). Briefly, blastocysts for injection were collected 4 d.p.c. from C57BL/6 donors, injected with 10-20 cells and allowed to re-expand in culture prior to transfer to the uteri of pseudopregnant recipients. Chimeras were identified by the presence of patches of sandy coat colour on the C57BL/6 background. Male chimeras were test bred for transmission of the Oct4-Neo transgene. Transgenic mice were then crossed onto different genetic backgrounds.

7. Results

The Oct4-Neo-βS construct generated approximately 50 colonies/$10^6$ cells transfected while the Oct4-Neo-βfos construct generated approximately 10 fold fewer colonies. Three clones were selected on the basis of their differential survival in medium containing G418 (200 µg/ml) in the presence or absence of DIA. All three cell lines displayed apparently normal growth rates in DIA-supplemented G418 containing media and died when cultured in the absence of DIA in G418 medium. Cultures maintained in DIA supplemented G418 medium grew as essentially pure ES cells while cultures maintained in DIA supplemented medium in the absence of G418 grew as mixed cultures of ES cells and differentiated progeny closely resembling those of the parental CGR-8 line. Thus G418 selection eliminates differentiated cell types and allows propagation of pure stem cell populations. The three cell lines selected were designated Oct4-Neo-βS18, Oct4-Neo-βS21 and Oct4-Neo-βfos11. These cell lines have been introduced into host blastocysts and resulting chimaeras may be test bred. Similar results were obtained with ES clones targetted with the Oct4-tgtvec construct. In addition, histochemical staining of these cultures for β-galactosidase activity confirmed that expression of βgeo was restricted to undifferentiated stem cells (Mountford et al, 1994).

Embryoid bodies were generated from the Oct4-Neo cell line Oct4-Neo-βpfos11 to examine the effect of G418 selection on mixed cell aggregates and to test the utility of the selection system in isolating ES cells from mixed cell populations. Embryoid bodies generated with both the experimental cell line (Oct4-Neo-βfos11) and the parental cell line (CGR-8) and cultured in the absence of G418 were composed almost entirely of differentiated cells with few if any ES like cells. In contrast, visual analysis of the expanded colonies revealed that the Oct4-Neo-βfos11 embryoid bodies cultured in the presence of G418 contained high proportions of ES cells. The feasibility of isolating stem cells from differentiating systems is thus confirmed.

8. Summary

ES cells capable of germ line transmission have previously been established from only 2 inbred strains of mice, 129 and C57BL/6. Combining the Oct4-neomycin selection scheme with established of ES cell isolation and propagation procedures (Evans and Kaufman, 1981; Martin, 1981; Nichols et al., 1990; Yoshida et al, 1994) should enable ES cell line derivation from previously non-productive mouse strains and other mammalian species in which Oct4 is differentially expressed.

Selection against non-stem cell phenotypes in mixed cell populations may be advantageous for several reasons. Firstly, selection against differentiated cells in mixed populations provides a method for extensive stem cell enrichment. Secondly, selective removal of differentiated cells prevents their overgrowth in the cultures. Thirdly, elimination of differentiated cells may enhance stem cell self-renewal due to the loss of differentiation inducing activity associated with differentiated cells.

EXAMPLE 2

Rescue And Recovery of Pluripotential Stem Cells From Es Cell Embryoid Bodies

Methods

1. Cell Culture

ES cells were routinely maintained in medium supplemented with Differentiation Inhibiting Activity (DIA) as described by Smith (1991). Embryoid bodies were formed by aggregation of ES cells in the absence of DIA. The aggregates were produced by plating dissociated ES cells in 10 μul or 30 μl drops of medium at a density of 100 cells/drop. Arrays of drops were plated on the lid of a 10 cm tissue culture dishes using a multipipettor. This was then inverted over the base of the dish, which contained 10 ml of water in order to maintain humidity, and the hanging drops were cultured at 37° C. in a 7% $CO_2$ atmosphere.

2. Histology and β-Galactosidase Staining

Embryoid bodies were fixed in Bouin's solution and embedded in agar. Paraffin sections were then prepared by standard procedures and stained with haematoxylin and eosin. Alkaline phophatase staining of embryoid body outgrowths was carried out using Sigma Kit 86-R. Histochemical staining for β-galactosidase was performed with Xgal as described (Beddington et al, 1986).

Results

3. Cell Lines and Selection System

Fos11 is a derivative of the ES cell line CGR8 which has been transfected with the Oct4neofos construct. Fos11 cells express low levels of G418 resistance under control of the Oct4 proximal promoter element, but differentiated progeny show no expression of the transgene and are therefore sensitive to G418. OKO160 and OKO8 are derivatives of the ES-cell lines CGR8 and E14TG2a respectively in which an IRES-βgeopA cassette has been introduced into one allele of the Oct4 gene by homologous recombination as described. OKO cell lines express high levels of βgeo in the undifferentiated state and therefore stain strongly with Xgal and are G418-resistant. Differentiated progeny lose expression of βgeo and become negative for Xgal staining and sensitive to G418. In monolayer cultures, Fos11 and OKO cells are maintained as pure ES cell populations by culture in the presence of DIA and selection in G418. Under conditions which favour differentiation, however, such as low density and absence of DIA (Smith, 1991), G418 selection results in the complete elimination of these cultures over 3-5 days. Rb4O cells are a derivative of CGR8 which are constitutively resistant to G418 due to expression of neoR directed by the human β-actin promoter.

4. Formation of Embryoid Bodies in the Presence and Absence of Selection against Differentiated Cells Production of embryoid bodies by the conventional procedure (Doetschman et al, 1986) of detachment of clumps of cells followed by aggregation in bulk suspension culture results in a mixed population of aggregates, heterogeneous in both size and differentiation status. In order to obtain more uniform and consistent development, embryoid bodies in the present study were formed by aggregation of defined numbers of cells in individual drops of culture medium (see Methods). After 48 hours in hanging drop culture, the aggregates were transferred en masse into suspension culture in the presence or absence of G418.

Under G418 selection against differentiated progeny aggregates still formed from both Fos11 cells and the OKO clones. Although some dead cells appeared around the periphery of the aggregates, the bodies themselves increased in size during the culture period. Samples were harvested periodically from the bulk cultures and processed for histological examination. After several days embryoid bodies formed in the absence of selection were mostly cystic and contained a variety of morphologically differentiated cell types. Undifferentiated cells were rarely apparent. By contrast, aggregates maintained under selection showed no indications of cellular specialisation and the bodies appeared to consist of solid balls of undifferentiated cells. The great majority of cells in these undifferentiated aggregates appeared healthy and viable and there was no evidence of necrosis, although occasional pyknotic nuclei, suggestive of apoptosis, were seen. Embryoid bodies formed in G418 were noticeably smaller than their counterparts formed in the absence of selection, however. This can be attributed to a combination of the lack of cyst development and the removal of differentiated cells.

5. Persistence of Pluripotential Stem Cells in Embryoid Bodies Formed Under Selection against Differentiated Cells.

The absence of any undifferentiated aggregates in control cultures implied that it was unlikely that the effect of G418 was due to selection of a subpopulation of non-differentiating aggregates. In order to exclude definitively this possibility, however, and also to facilitate quantitative determination of the effects of G418 selection, a modified protocol was used which allows assessment of the behaviour of individual aggregates. Cultures were initiated in 30μl hanging drops in the presence or absence of G418 and maintained in drop culture for 7-8 days. Embryoid bodies were then transferred individually to gelatin-coated 96-well tissue culture plates and the media diluted 6-fold with media lacking G418. The stem cell maintenance factor DIA was added at this stage to allow expansion of any undifferentiated ES cells which were present. The cultures were allowed to attach and outgrow for 48 hours then fixed and stained for alkaline phosphatase or for p-galactosidase as appropriate.

The data summarized in Table 1 show that in the absence of any selection undifferentiated stem cells are almost completely eliminated from embryoid bodies within 7 days of suspension culture. Outgrowths contained a variety of morphologically differentiated cell types, but areas of cells with ES cell morphology were not observed. In the OKO cells expression of p-galactosidase is coupled to the stem cell-specific transcription factor Oct4 (Mountford et al, 1994) and therefore serves as a marker of undifferentiated cells. Isolated Xgal-staining cells were occasionally seen in OKO outgrowths, but clusters of staining cells were not detected under these conditions (but see Discussion).

The efficiency of embryoid body formation in G418 was identical to that in non-selected cultures, essentially 100%. In marked contrast to the untreated embryoid bodies, however, embryoid bodies established under continuous G418 selection gave rise to outgrowths consisting largely of ES cells. The undifferentiated nature of these cells was indicated by the characteristic morphology of ES cell colonies and by staining with alkaline phosphatase and was confirmed by Xgal staining of the OKO outgrowths.

Several outgrowths from embryoid bodies formed under selection were picked and transferred to 2 cm wells. All of the colonies picked were readily expanded into mass cultures of undifferentiated cells. These cultures remained dependent on DIA and differentiated in similar fashion to parental ES cells when plated in non-supplemented media. Furthermore, these derivatives differentiated efficiently into multiple cell types on aggregation, confirming their pluripotency.

These findings demonstrate that the selective elimination of differentiated progeny results in the persistence of pluripotential stem cells in ES cell aggregates.

6. Stem Cell Extinction in Mixed Aggregates

The implication that differentiated progeny may be directly responsible for stem cell extinction in embryoid bodies was addressed further. The behaviour of OKO cells was assessed following formation of mixed aggregates with Rb4O ES cells which can differentiate in the presence of G418. Rb4O cells express neomycin phosphotransferase constitutively and G418 selection has no discernible effect on their differentiation, either in monolayer culture or in aggregates. Hanging drop cultures were established using a 3:1 ratio of OKO cells to Rb40 cells. Paraffin sections of mixed embryoid bodies revealed that they underwent extensive differentiation in both the absence and the presence of G418. The effective elimination of undifferentiated stem cells under both conditions was confirmed by Xgal-staining of outgrowths (Table 1).

This result provides direct evidence that the presence of differentiated progeny induces the elimination of pluripotential stem cells. This implies that certain differentiated stem cell progeny are a source of inductive signals which either instruct further differentiation of remaining stem cells or possibly induce them to enter apoptosis.

CONCLUSION

Aggregation induces ES cells to develop into differentiated structures known as embryoid bodies. Pluripotential stem cells rapidly become extinct in these embryoid bodies due to the efficient induction of differentiation and possibly also to selective cell death. However, if differentiated progeny are specifically eliminated from the aggregates using methods according to the invention, the stem cells persist and can be propagated.

The findings detailed above constitute a clear demonstration that through the use of a stem cell-specific selection system according to the invention it is possible to recover stem cells from conditions which would normally force their elimination by either differentiation or death.

TABLE 1

Disappearance of Persistence of Oct-4 Expressing ES Cells in Embryoid Bodies.

| Culture | G418* | No Drops | No. Outgrowths | No. Xgal +ve | % +ve Drops |
|---|---|---|---|---|---|
| OKO8 | − | 25 | 25 | 0 | 0 |
| OKO8 | + | 25 | 24 | 24 | 96 |
| OKO160 | − | 30 | 30 | 0 | 0 |
| OKO160 | + | 30 | 30 | 30 | 100 |
| OKO160:Rb40 | − | 30 | 29 | 0 | 0 |
| OKO160:Rb40 | + | 30 | 30 | 0 | 0 |

*500 μg/ml

EXAMPLE 3

Procedures for Establishing Embryonic Stem Cell Cultures from Mouse Embryos

Lines of transgenic mice were established in which the neomycin phosphotransferase gene conferring resistance to G418 is expressed with the specificty of the Oct4 gene. The βS21 line harbour the Oct4neoμS transgene whilst in the OKO line the neo gene has been incorporated into the endogenous Oct gene via gene targeting with the Oct4-tgtvec construct. These mice were outcrossed for two generations with MF1 outbred albino mice and with inbred CBA mice. Neither of these mouse strains produce ES cells using standard procedures.

Four preferred procedures for isolating stem cells are described. In all cases the embryos are cultured in standard ES cell culture medium supplemented with either Differentiation Inhibiting Activity (Smith, 1991) or interleukin-6 plus soluble interleukin-6 receptor (Yoshida et al, 1994). G418 is added at concentrations of 200 μg/ml-1 mg/ml.

Procedure 1

Blastocysts are flushed on the fourth day of pregnancy. Groups of 4-10 blastocysts are cultured in 1 cm tissue culture wells under G418 selection. Outgrowths are individually detached and dissociated with trypsin as described (Nichols et al, 1990) after 4-6 days in culture and replated in single wells. G418 selection is maintained. Colonies with the characteristic morphology of ES cells which appear in the cultures over the next 14 days are picked and expanded under continuous selection.

Procedure 2

As Procedure 1, except that blastocysts are put into implantation delay before harvesting by ovariectomy of the dams on the third day of pregnancy. Blastocysts are flushed 4 days after the ovariectomy.

Procedure 3

Post-implantation embryos between 5.5 and 7.5 days post-coitum are isolated and the primitive ectoderm separated by microdissection and/or protease digestion. The primitive ectoderm is gently dissociated into clumps of 20-50 cells which are then cultured as in Procedure 1.

Procedure 4

Embryos prepared as for Procedures 1, 2 or 3 are cultured in hanging drops under G418 selection for a period of 5-7 days before transfer to tissue culture wells and subsequent manipulation as in Procedure 1.

The invention claimed is:

1. A method of preparing a transgenic non-human mammal comprising:
    a) obtaining a desired stem cell by:
        i) culturing non-human mammalian embryonic stem (ES) cells containing a nucleic acid construct including a selectable marker operably linked to a promoter that preferentially expresses the selectable marker in mammalian ES cells; and
        ii) isolating mammalian ES cells expressing the selectable marker; and
    b) generating the transgenic non-human mammal therefrom.

2. A method of preparing a transgenic non-human mammal, said mammal comprising a selectable marker operatively linked to a promoter that preferentially expresses the selectable marker in mammalian ES cells, the method comprising:

a) providing a blastocyst;
b) providing a non-human mammalian ES cell comprising at least one nucleic acid construct encoding a selectable marker operably linked to a promoter which preferentially expresses said marker in a mammalian ES cell;
c) introducing the mammalian ES cell into the blastocyst;
d) transferring the blastocyst to a recipient; and
e) allowing an embryo to develop to a chimeric mammal to enable germline transmission of the selectable marker.

3. The method of claim 2, wherein the mammalian stem cells are mouse stem cells.

4. The method of claim 2, wherein the promoter is an Oct4 promoter.

5. The method of claim 2, wherein the selectable marker is a gene product that allows purification of said mammalian ES cells by fluorescent-activated cell sorting (FACS).

6. The method of claim 2, wherein the selectable marker is a fluorescent marker.

7. The method of claim 2, wherein the selectable marker is a cell surface antigen.

8. The method of claim 2, wherein the selectable marker is a growth factor receptor.

9. The method of claim 2, wherein the selectable marker is an antibiotic resistance gene.

10. The method of claim 9, wherein the antibiotic resistance gene is a neomycin phosphotransferase gene.

11. A method of isolating non-human mammalian ES cells from a population of non-human mammalian cells, comprising:
a) obtaining cells from a transgenic non-human mammal prepared using the method of claim 1 or claim 2, wherein the mammalian cells contain a nucleic acid construct including a selectable marker operably linked to a promoter that preferentially expresses the selectable marker in mammalian ES cells;
b) culturing said mammalian ES cells; and
c) isolating mammalian ES cells expressing the selectable marker.

12. The method of claim 11, wherein the cells obtained from the transgenic non-human mammal are derived from an embryo.

* * * * *